(12) United States Patent
Okoniewski

(10) Patent No.: US 8,403,837 B2
(45) Date of Patent: Mar. 26, 2013

(54) DEPLOYABLE JAWS RETRACTION DEVICE

(75) Inventor: Gregory Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 318 days.

(21) Appl. No.: 12/791,012

(22) Filed: Jun. 1, 2010

(65) Prior Publication Data

US 2011/0040153 A1    Feb. 17, 2011

Related U.S. Application Data

(60) Provisional application No. 61/233,618, filed on Aug. 13, 2009.

(51) Int. Cl.
*A61B 1/32* (2006.01)
(52) U.S. Cl. .......................... 600/201; 600/218; 600/235
(58) Field of Classification Search .................. 600/201, 600/206, 209, 217, 218; 606/99, 138–141, 606/151, 153, 157, 206
See application file for complete search history.

(56) References Cited

U.S. PATENT DOCUMENTS

| | | |
|---|---|---|
| 1,274,669 A | 8/1918 | Bohn |
| 2,549,731 A | 12/1944 | Wattley |
| 3,404,677 A | 10/1968 | Springer |
| 3,809,094 A | 5/1974 | Cook |
| 3,877,434 A | 4/1975 | Ferguson et al. |
| 3,994,287 A | 11/1976 | Turp et al. |
| 4,046,149 A | 9/1977 | Komiya |
| 4,051,844 A | 10/1977 | Chiulli |
| 4,174,715 A | 11/1979 | Hasson |
| 4,177,813 A | 12/1979 | Miller et al. |
| 4,374,523 A | 2/1983 | Yoon |
| 4,393,872 A | 7/1983 | Reznik et al. |
| 4,519,392 A | 5/1985 | Lingua |
| 4,605,990 A | 8/1986 | Wilder et al. |
| 4,607,620 A | 8/1986 | Storz |
| 4,617,933 A | 10/1986 | Hasson |
| 4,681,107 A | 7/1987 | Kees, Jr. |
| 4,706,668 A | 11/1987 | Backer |
| 4,777,949 A | 10/1988 | Perlin |
| 4,779,616 A | 10/1988 | Johnson |
| 4,796,626 A | 1/1989 | DeVries |
| 4,932,955 A | 6/1990 | Merz et al. |
| 4,950,273 A | 8/1990 | Briggs |

(Continued)

FOREIGN PATENT DOCUMENTS

| | | |
|---|---|---|
| DE | 26 04 024 A1 | 8/1976 |
| EP | 2 127 606 A1 | 12/2009 |

(Continued)

OTHER PUBLICATIONS

European Search Report for corresponding EP 10 25 1436 application, date of completion is Nov. 9, 2010 (3 pages).

*Primary Examiner* — Kevin T Truong
*Assistant Examiner* — Christian Sevilla

(57) ABSTRACT

A deployable jaws retraction device is provided for retracting a body organ away from an operative site without occupying an incision or surgical access port during the surgical procedure. The deployable jaws retraction device includes a jaw assembly having two or more jaws joined at one end and a retention device to maintain the jaws of the closed condition about a target body organ. The deployable jaws retraction device additionally includes an anchoring assembly for securing the jaw assembly and body organ away from the operative site during the surgical procedure. The anchoring assembly includes a needle having a tissue penetrating tip and a length of suture material connecting the needle to the jaw assembly. There is also provided an applicator instrument for applying the deployable jaws retraction device onto a target body organ.

7 Claims, 3 Drawing Sheets

U.S. PATENT DOCUMENTS

| | | |
|---|---|---|
| 4,988,355 A | 1/1991 | Leveen et al. |
| 4,990,157 A | 2/1991 | Roberts et al. |
| 5,022,693 A | 6/1991 | Loveless |
| 5,059,202 A | 10/1991 | Liang et al. |
| 5,074,869 A | 12/1991 | Daicoff |
| 5,074,870 A | 12/1991 | Von Zeppelin |
| 5,100,417 A | 3/1992 | Cerier et al. |
| 5,201,714 A | 4/1993 | Gentelia et al. |
| 5,242,456 A | 9/1993 | Nash et al. |
| 5,261,895 A | 11/1993 | Kablik |
| 5,282,806 A | 2/1994 | Haber et al. |
| 5,304,183 A | 4/1994 | Gourlay et al. |
| 5,415,666 A | 5/1995 | Gourlay et al. |
| 5,658,298 A | 8/1997 | Vincent et al. |
| 5,669,883 A | 9/1997 | Scarfone et al. |
| 5,690,676 A | 11/1997 | DiPoto et al. |
| 5,795,325 A | 8/1998 | Valley et al. |
| 5,893,873 A | 4/1999 | Rader et al. |
| 5,893,874 A | 4/1999 | Bourque et al. |
| 5,899,853 A | 5/1999 | Fowler, Jr. |
| 5,911,702 A | 6/1999 | Romley et al. |
| 5,921,979 A | 7/1999 | Kovac et al. |
| 5,921,996 A | 7/1999 | Sherman |
| 5,925,052 A | 7/1999 | Simmons |
| 5,954,057 A | 9/1999 | Li |
| 5,976,069 A | 11/1999 | Navia et al. |
| 6,013,088 A | 1/2000 | Karavidas |
| 6,182,664 B1 | 2/2001 | Cosgrove |
| 6,206,827 B1 | 3/2001 | Chin et al. |
| 6,251,093 B1 | 6/2001 | Valley et al. |
| 6,383,199 B2 | 5/2002 | Carter et al. |
| 6,539,945 B2 | 4/2003 | Cosgrove |
| 6,610,074 B2 | 8/2003 | Santilli |
| 6,732,739 B2 | 5/2004 | Cosgrove |
| 7,107,124 B2 | 9/2006 | Green |
| 7,118,582 B1 | 10/2006 | Wang et al. |
| 7,137,988 B2 | 11/2006 | Frye |
| 7,229,465 B2 | 6/2007 | Burbank et al. |
| 2003/0109900 A1 | 6/2003 | Martinek |
| 2006/0224165 A1* | 10/2006 | Surti et al. .................. 606/142 |
| 2009/0306686 A1 | 12/2009 | Ohdaira |

FOREIGN PATENT DOCUMENTS

| | | |
|---|---|---|
| WO | WO 93/18712 | 9/1993 |
| WO | WO 03/030746 | 4/2003 |
| WO | WO 2007/142977 | 12/2007 |
| WO | WO 2008/001882 A | 1/2008 |
| WO | WO 2008/090978 | 7/2008 |

* cited by examiner

DEPLOYABLE JAWS RETRACTION DEVICE

CROSS REFERENCE TO RELATED APPLICATION

The present application claims the benefit of and priority to U.S. Provisional Application Ser. No. 61/233,618 filed on Aug. 13, 2009, the entire contents of which are incorporated herein by reference.

BACKGROUND

1. Technical Field

The present disclosure relates to a deployable jaws retraction device. More particularly, the present disclosure relates to a retraction device for engaging and retracting an organ within a body cavity and an applicator instrument for positioning the retraction device about the organ.

2. Background of Related Art

Many surgical procedures are currently performed in a minimally invasive manner so as to limit the amount of trauma to the patient and promote more rapid healing. These minimally invasive procedures generally include forming one or more incisions through the body wall of a patient and inserting the operative surgical instruments through the incisions. In some instances, access ports are inserted through the incisions and are provided to receive surgical instruments therethrough. In some surgical procedures, it is often necessary to move or retract a portion of the body, such as a body organ, away from the operative site to facilitate performing the surgery. This is often accomplished by inserting an elongate retraction instrument through the incision or access port and utilizing movable jaw structure located at a distal end of the surgical instrument to grasp the body organ and move or retract the body organ away from the operative site.

In these methods of retracting body organs, the elongate retraction instrument remains positioned through the body wall and occupies the incision or access port during the entire surgical procedure. In complex surgical procedures, multiple incisions or access ports are required to accommodate the multiple surgical instruments used during the surgical procedures. Each incision or access port utilized in the surgical procedure contributes to the degree of trauma and rate of healing of the patient.

Therefore, it is desirable to provide retraction device assembly including an applicator instrument and a deployable retraction device which can be inserted through a surgical incision or access port to engage and retract a body organ while allowing for removal of the applicator instrument from the incision or access port during the surgical procedure so as to limit the number of incisions or access ports required.

SUMMARY

There is provided a deployable jaws retraction device having a jaw assembly including a first flexible jaw having a first distal end and a first proximal end and a second flexible jaw having a second distal end and a second proximal end. The first proximal end of the first jaw is connected to the second proximal end of the second jaw at a junction. The jaw assembly additionally includes a retainer engageable with the first and second flexible jaws. The first flexible jaw and the second flexible jaw are movable between a closed constrained condition and an open unconstrained condition.

The retainer is an O-ring positionable over the first and second flexible jaws to maintain the first and second flexible jaws in the closed constrained condition. The first flexible jaw and the second flexible jaw each include a recess for receipt of the O-ring.

In a specific embodiment, the deployable jaws retraction device further includes a third flexible jaw having a third proximal end and a third distal end. The third proximal end of the third flexible jaw is connected to the first and second proximal ends of the first and second flexible jaws at the junction. The third flexible jaw also includes a recess for receipt of the O-ring. In a more specific embodiment, the first proximal end, the second proximal end and the third proximal end are spaced apart 120° at the junction. In a particular embodiment, the first flexible jaw, the second flexible jaw and the third flexible jaw each have an arcuate configuration.

The deployable jaws retraction device further includes an anchor assembly for securing the retraction device away from an operative site. The anchor assembly includes a surgical needle having a tissue penetrating tip. The anchor assembly further includes a length of suture material connecting the surgical needle to the jaw assembly. The length of suture material is connected to the jaw assembly at the junction.

There is also disclosed a surgical retraction assembly having a deployable retraction device including a pair of jaws engageable with a target body organ and a retainer maintaining the pair of jaws in engagement with the target body organ. The surgical retraction assembly additionally includes an applicator instrument for insertion of the deployable retraction device through a body wall and position the deployable retraction device about the target body organ.

The applicator instrument includes an inner tube for receipt of the deployable retraction device and a pusher engageable with the deployable retraction device and movable through the inner tube to eject the deployable retraction device from the inner tube. The applicator instrument also includes an outer tube surrounding the inner tube and defining a space between the inner and outer tubes. The inner tube and the outer tube are connected together at an end cap.

The retainer is positioned within the space located between the inner and outer tubes. An ejection device is provided within the applicator instrument and is movable within the space and engageable with the retainer to drive the retainer over the pair of jaws to maintain the jaws in a closed condition about the target body organ.

In a specific embodiment, the ejection device includes at least one ring rod movable within the space and engageable with the retainer.

In an alternative embodiment, the ejection device includes an ejection tube movable within the space and engageable with the retainer.

There is further disclosed a method of retracting a target body organ away from an operative site. The method includes providing a deployable jaws retraction device having a jaw assembly including a first flexible jaw and a second flexible jaw secured together at respective proximal ends and a retainer engageable with the first flexible jaw and the second flexible jaw to maintain the first and second flexible jaws in a closed condition about the target body organ.

In the disclosed method, the deployable jaws retraction device is positioned within an applicator instrument in a closed constrained condition and the applicator instrument is inserted into the body of a patient such that the deployable jaws retraction device is positioned adjacent the target body organ. The deployable jaws retraction device is advanced out of the applicator instrument such that the deployable jaws retraction device expands from the closed constrained condition to an open condition.

The first flexible jaw and the second flexible jaw of the deployable jaws retraction device are positioned about the target body organ and the first flexible jaw and the second flexible jaw are moved to the closed constrained condition about the target organ by advancing a retainer over the first flexible jaw in the second flexible jaw.

DESCRIPTION OF THE DRAWINGS

An embodiment of the presently disclosed deployable jaws retraction device and applicator instrument is disclosed herein with reference to the drawings, wherein.

DETAILED DESCRIPTION OF EMBODIMENTS

An embodiment of the presently disclosed deployable jaws retraction device assembly will now be described in detail with reference to the drawings wherein like numerals designate identical or corresponding elements in each of the several views. As is common in the art, the team 'proximal" refers to that part or component closer to the user or operator, i.e. surgeon or physician, while the term "distal" refers to that part or component further away from the user.

Figure 1:
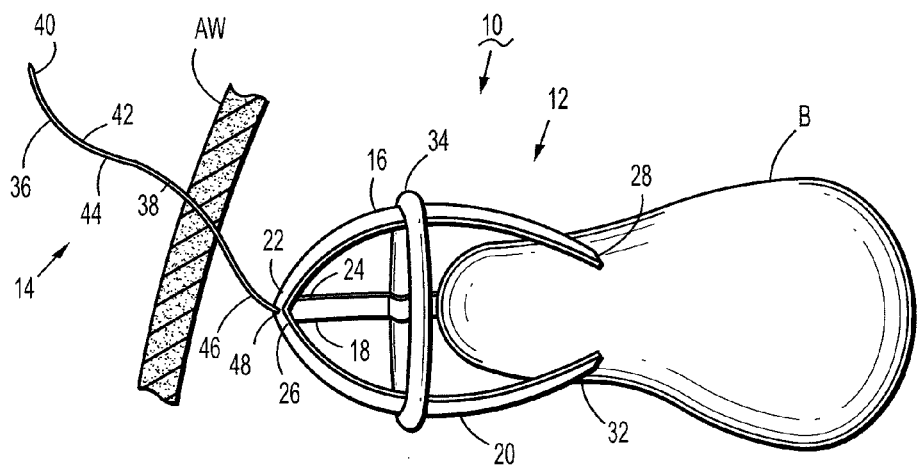
FIG. 1 is a perspective view of a deployable jaws retraction device engaging a body organ and retracting the organ adjacent an abdominal wall.

Referring initially to FIG. 1, there is disclosed a deployable jaws retraction device or retraction device 10 which generally includes a jaw assembly 12 and an anchoring assembly 14 affixed to jaw assembly 12. Jaw assembly 12 is provided to engage and retract a body organ such as body organ B and anchoring assembly 14 is provided to retract body organ B and retain body organ B away from an operative site adjacent an alternative body structures such as, for example, abdominal wall AW.

Jaw assembly 12 includes a first jaw 16, a second jaw 18 and third jaw 20. First jaw 16 includes a first proximal end 22 and second jaw 18 includes a second proximal end 24. First proximal end 22 of first jaw 16 is connected to second proximal end 24 of second jaw 18. Third jaw 20 additionally includes a third proximal end 26 which is also connected to first proximal end 22 of first jaw 16 and second proximal end 24 of second jaw 18. First jaw 16, second jaw 18 and third jaw 20 include respective first distal end 28, second distal end 30 and third distal end 32.

Jaw assembly 12 is provided to initially be restrained within a surgical instrument, described in more detail hereinbelow, in a stressed condition and deployed outside of the surgical instrument to An unstressed condition for surrounding and engaging body organ B. First jaw 16, second jaw 18 and third jaw of 20 are formed in an arcuate shape or configuration so as to surround the body organ B. It should be noted that, two of the jaws such as, for example, first jaw 16 and third jaw 20 may be formed integrally from a single length of material and the last jaw such as, for example, second jaw 18 affixed to first jaw 16 and third jaw 20.

First jaw 16, second jaw 18 and third jaw 20 are formed from a flexible material to allow them to move from a stressed or constrained condition when positioned within the surgical instrument to an open unstressed or unconstrained condition when deployed from the surgical instrument. The disclosed flexible materials may include various compatible materials such as, for example, spring steels, shape memory alloys, plastics or polymers, etc.

Jaw assembly 12 additionally includes a retention device such as, for example, O-ring 34 which is engageable with and positionable over first jaw 16, second jaw 18 and third jaw 20 to maintain the jaws in a closed position about the body organ B.

As noted hereinabove, retraction device 10 additionally includes an anchoring assembly 14 for securing jaw assembly 12 and an associated body organ BO adjacent an abdominal wall AW. Anchoring assembly 14 generally includes a surgical needle 36 having a length of suture material 38 affixed to surgical needle 36. Surgical needle 36 includes a tissue penetrating tip 40 for piercing abdominal wall AW. A tag end 42 of surgical needle 36 is connected to a first end 44 of length of suture material 38. A second end 46 of length of suture material 38 is connected to a junction 48 formed by the connection of first proximal end 22, second proximal end 24 and third proximal end 26 of respective first jaw 16, second jaw 18 and third jaw 20.

It should be noted that, first proximal end 22, second proximal end 24 and third proximal end 26 are spaced apart 120° from each other at junction 48 to allow first jaw 16, second jaw 18 and third jaw 20 to evenly surround and grasp body organ B.

As noted hereinabove, tissue penetrating tip 40 is provided to pierce abdominal wall AW allowing surgical needle 36 to pass through abdominal wall AW. Drawing surgical needle 40 through abdominal wall AW also draws length of suture material 38 through abdominal wall AW such the jaw assembly 12, having body organ BO engaged by jaw assembly 12, is drawn toward or retracted against abdominal wall AW.

Figure 2:
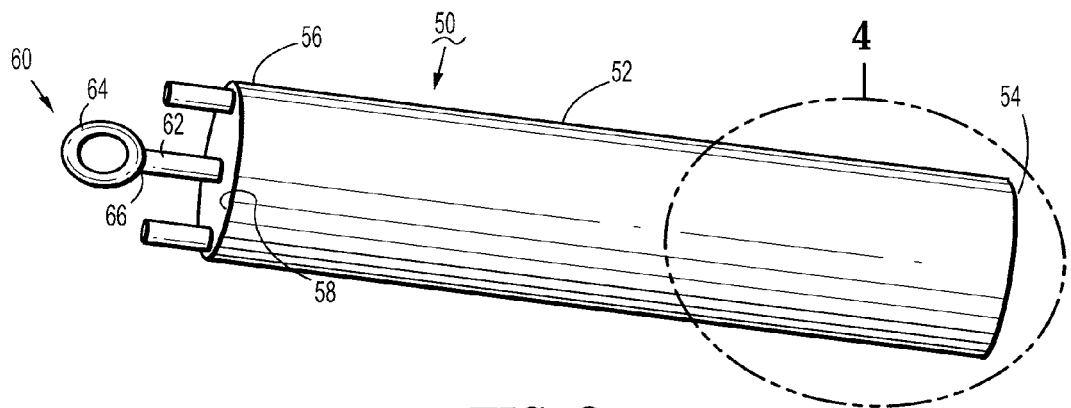
FIG. 2 is a perspective view of an applicator instrument for positioning the deployable jaws retraction device about the body organ.
Figure 3:
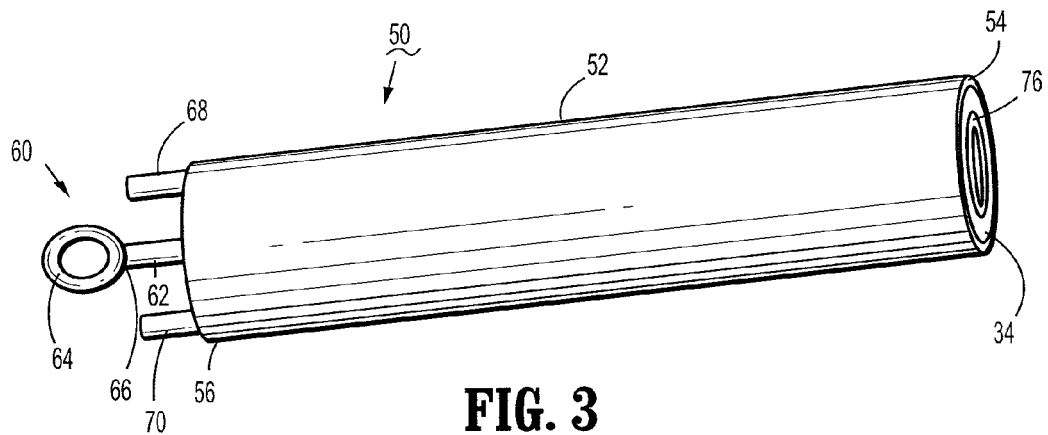
FIG. 3 is a another perspective view of the applicator instrument.

Referring now to FIGS. 2-5, and initially with regard to FIGS. 2 and 3, there is disclosed an applicator instrument 50 for retaining retraction device 10 during insertion through the abdominal wall AW and deploying retraction device 10 about body organ B. Applicator instrument 50 includes an outer tube 52 having an open distal end 54 and a closed proximal end 56 including an end cap 58. A pusher 60 is provided to eject the retraction device 10 from applicator instrument 50 and includes a push rod 62, extending through end cap 58, and a handle ring 64 located at a proximal end 66 of push rod 62. First and second ring rods 68 and 70, respectively, also extend through end cap 58 and are provided to drive O-ring 34 out of applicator instrument 50 and over first jaw 16, second jaw 18 and third jaw 20 to secure the jaws about body organ B.

Figure 4:
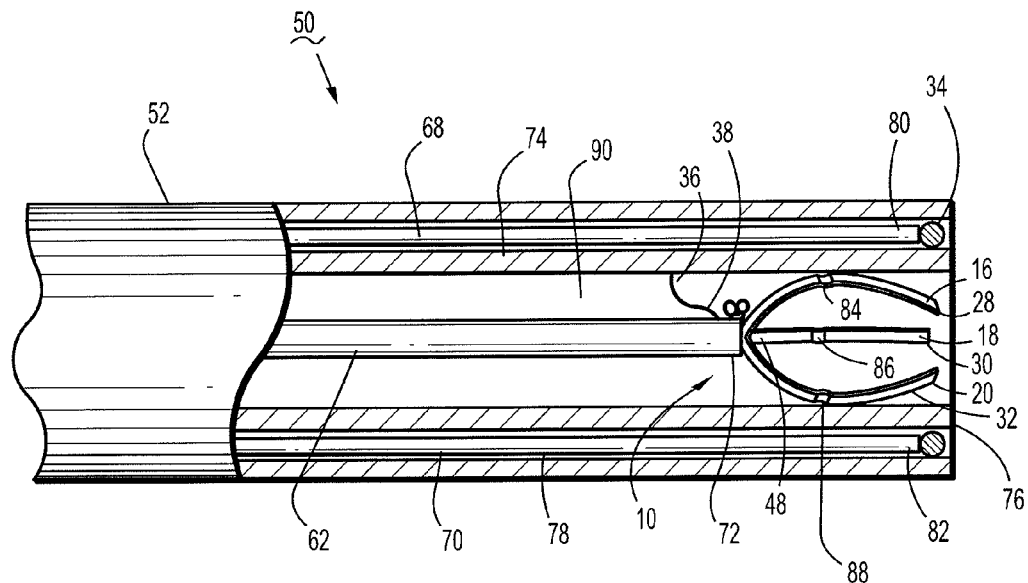
FIG. 4 is a perspective view, partially shown in section, of the distal end of the applicator instrument.
Figure 5:
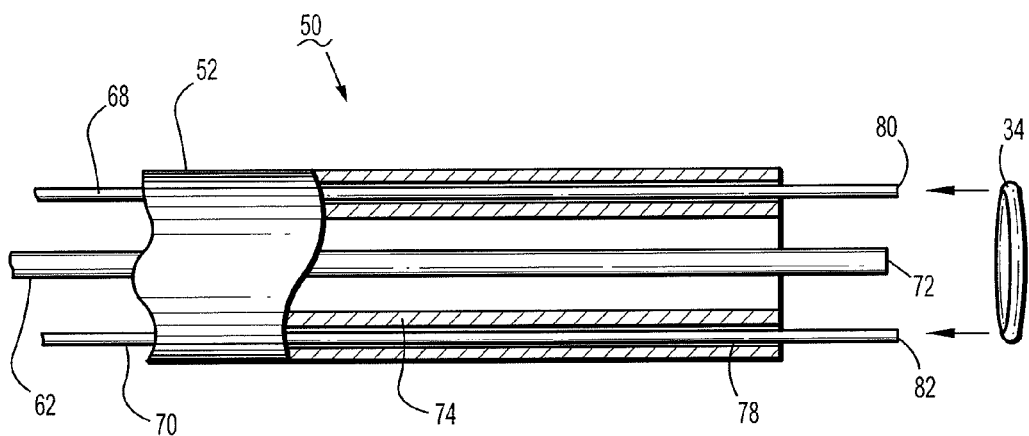
FIG. 5 is a perspective view, partially shown in section, of the applicator instrument illustrating movement of a retention ring out of the applicator instrument.

Referring now to FIGS. 4 and 5, and as noted hereinabove, pusher 60, and specifically push rod 62, is provided to eject first jaw 16, second jaw 18 and third jaw 20 out of applicator instrument 50 so as to be positioned about a body organ B.

Specifically, a distal end 72 of push rod 62 is provided to engage junction 48 of first, second, and third jaws 16, 18 and 20 respectively (FIG. 4).

Applicator instrument 50 additionally includes an inner tube 74 having an open distal end 76. A proximal end (not shown) of inner tube 74 is affixed to end cap 58. As shown, first and second ring rods 68 and 70 extend through a space 78 formed between inner tubes 74 and outer tube 52. As best seen in FIG. 4, O-ring 34 is initially retained within space 78 and adjacent a distal end 80 of first ring rods 68 and a distal and 82 of second ring rods 70. Thus, movement of first and second ring rods 68 and 70 through space 78 forces O-ring 34 out of space 78 to be positioned over first jaw 16, second jaw 18 and third jaw 20.

Referring for the moment to FIG. 4, in order to maintain O-ring 34 in engagement with first jaw 16, second jaw 18 and third jaw 20, first jaw 16 includes a first recess 84 located between first distal end 28 and junction 48 and second jaw 18 includes a second recess 86 located between second distal end 30 and junction 48. Similarly, third jaw 20 includes a recess 88 located between third distal end 32 and junction 48. Recesses 84, 86 and 88 are provided to receive O-ring 34 and retain O-ring 34 on first jaw 16, second jaw 18 and third jaw 20 so as to maintain the jaws in the closed position.

Referring now to FIGS. 2, 4 and 6-9, the use of applicator instrument 50 to deploy retraction device 10 about body organ B will now be described. Initially, with regard to FIG. 4, retraction device 10 is positioned within a bore 90 of inner tube 74. First jaw 16, second jaw 18 and third jaw 20 are in a constrained condition within bore 90. As noted hereinabove, junction 48 is positioned adjacent distal end 72 of push rod 62. O-ring 34 is located within space 78 and adjacent distal ends 80 and 82 of first and second ring rods 68 and 70.

Figure 6:
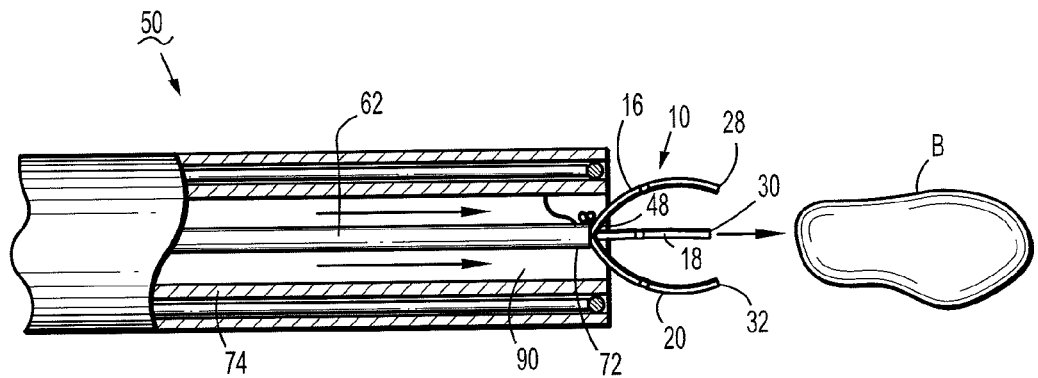
FIG. 6 is a perspective view, partially shown in section, illustrating the initial advancement of the deployable jaws retention device toward a body organ.

In use, while not specifically shown, applicator instrument 50, containing retraction device 10, is inserted through an incision or access port formed in an abdominal wall. Applicator instrument 50 is manipulated to position retraction device 10 adjacent a body organ B. Referring now to FIGS. 2 and 6, once applicator instrument 50 has been properly positioned relative to body organ B, handle ring 64 of pusher 60 is advanced through end cap 58 (FIG. 2) thereby driving pushrod 62 distally through bore 90 of inner tube 74. As pushrod 62 moves distally throughbore 90, distal end 72 of pushrod 62 engages junction 48 to drive first jaw 16, second jaw 18 and third jaw 20 out of bore 90. Upon exiting bore 90, first jaw 16, second jaw 18 and third jaw 20 move or flex outwardly from the constrained condition to an expanded condition such that distal ends 28, 30 and 32 of first jaw 16, second jaw 18 and third jaw 20, respectively, are sufficiently spaced apart to surround the target body organ B.

Figure 7:
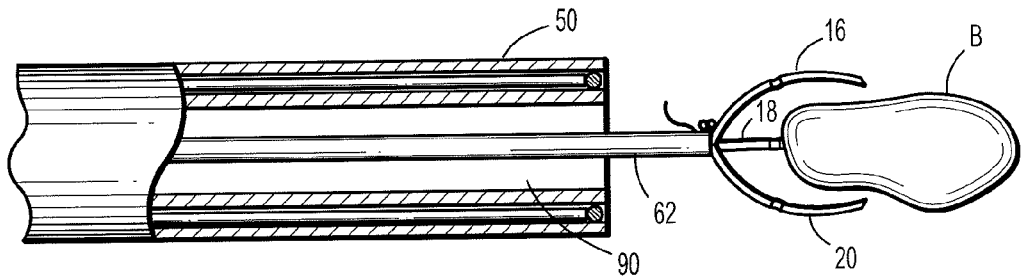
FIG. 7 is a perspective view, partially shown in section, illustrating the positioning of a jaw assembly of the deployable jaws retention device about the body organ.
Figure 8:
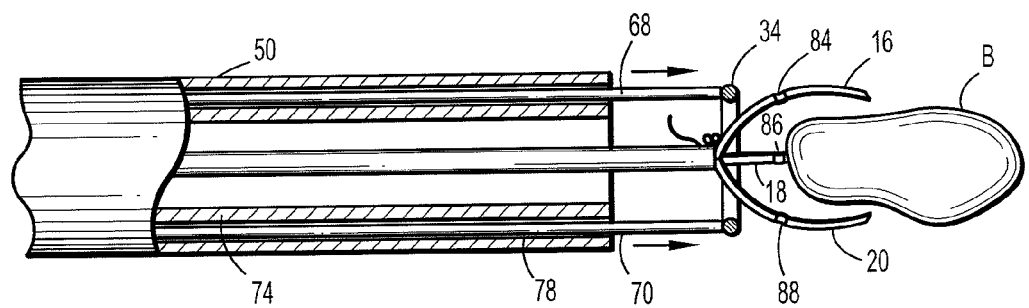
FIG. 8 is a perspective view, partially shown in section, illustrating the advancement of the retention ring about the jaw assembly.
Figure 9:
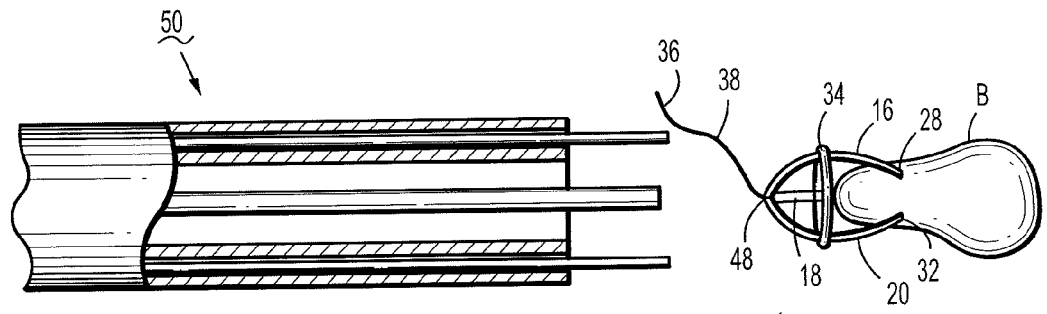
FIG. 9 is a perspective view, partially shown in section, illustrating the engagement of the deployable jaws retention device with the body organ.

Referring now to FIG. 7, pushrod 62 continues to be advanced through applicator instrument 50 to position first jaw 16, second jaw 18 and third jaw 20 about body organ B. With reference to FIG. 8, thereafter, ring rods 68 and 70 are advanced distally to drive O-ring 34 out of space 78 between outer tube 52 and inner tube 74. O-ring 34 continues to be advanced distally over first jaw 16, second jaw 18 and third jaw 20 forcing the jaws to move together so as to capture body organ B. O-ring 34 is advanced a sufficient distal distance so as to be positioned within recesses 84, 86 and 88 in first jaw 16, second jaw 18 and third jaw 20, respectively, so as to secure the jaws about body organ B (see FIG. 9).

Thereafter, applicator instrument 50 can be removed back through the incision or access port to free up the incision or access port for insertion of a subsequent surgical instrument. Referring for the moment back to FIG. 1, surgical needle 36 is manipulated to drive tissue penetrating tip 40 through abdominal wall AW. Surgical needle 36 is drawn through abdominal wall AW pulling length of suture material 38, and thus jaw assembly 12 including body organ B, adjacent abdominal wall AW and away from the operative site. In this manner, applicator instrument 50 along with retraction device 10 allow body organ B to be retracted away from the operative site without the need for an additional surgical incision or access port.

It will be understood that various modifications may be made to the embodiments disclosed herein. For example, the disclosed jaw assembly may include more or less than three jaws. Further, alternative retention devices may be provided to secure the jaws in a closed condition such as, for example, clips, lengths of suture, tubular shields, etc. Additionally, the disclosed applicator instrument may include other methods of anchoring the disclose jaw of assembly to an abdominal wall such as, for example, staples, barbed tacks, etc. Therefore, the above description should not be construed as limiting, but merely as exemplifications of particular embodiments. Those skilled in the art will envision other modifications within the scope and spirit of the claims appended hereto.

The invention claimed is:

1. A method of retracting a target body organ away from an operative site comprising:
   providing a deployable jaws retraction device having a jaw assembly including a first flexible jaw and a second flexible jaw secured together at respective first and second proximal ends at a junction; and
   a retainer engageable with the first flexible jaw and the second flexible jaw to maintain the first and second flexible jaws in a closed condition about the target body organ;
   positioning the deployable jaws retraction device, in a closed constrained condition, within an applicator instrument and inserting the applicator instrument into the body of a patient such that the deployable jaws retraction device is positioned adjacent the target body organ;
   advancing the deployable jaws retraction device out of the applicator instrument while maintaining the retainer within the applicator instrument such that the deployable jaws retraction device expands from the closed constrained condition to an open condition;
   positioning the first flexible jaw and the second flexible jaw of the deployable jaws retraction device about the target body organ; and
   moving the first flexible jaw and the second flexible jaw to the closed constrained condition about the target organ by advancing the retainer over the first flexible jaw and the second flexible jaw; piercing an abdominal wall with a tissue penetrating tip attached to a length of suture material and drawing the suture material through the abdominal wall such that the body organ is drawn toward the abdominal wall.

2. The method according to claim 1, wherein the retainer is in the form of an O-ring that is positionable over the first and second flexible jaws.

3. The method according to claim 2, including maintaining the first and second flexible jaws in the closed constrained condition by advancing the O-ring into recesses on the first and second flexible jaw members.

4. The method according to claim 1, further including providing a third flexible jaw having a third proximal end and a third distal end, wherein the third proximal end of the third flexible jaw is connected to the first and second proximal ends of the first and second flexible jaws at the junction.

5. The method according to claim 4, wherein the third flexible jaw includes a recess for receipt of the retainer.

6. The method according to claim 4, including spacing the first proximal end, the second proximal end and the third proximal end 120° apart from one another.

7. The method according to claim 1, including providing the first flexible jaw and the second flexible jaw with an arcuate configuration.

* * * * *